United States Patent [19]

Liu

[11] Patent Number: 5,320,844

[45] Date of Patent: Jun. 14, 1994

[54] COMPOSITE MATERIALS FOR HARD TISSUE REPLACEMENT

[76] Inventor: Sung-Tsuen Liu, 29 Landing, Laguna Niguel, Calif. 92677

[21] Appl. No.: 849,880

[22] Filed: Mar. 12, 1992

[51] Int. Cl.$^5$ ............................................. A61F 2/02
[52] U.S. Cl. ................................... 424/422; 424/424; 424/426; 424/602; 523/115; 523/116
[58] Field of Search ................. 623/16; 424/422, 424, 424/602, 423, 426; 523/115, 116

[56] References Cited

U.S. PATENT DOCUMENTS 4,623,553 11/1986 Ries et al. ................................ 62/16
4,888,366 12/1989 Chu et al. ............................. 623/16
5,034,352 7/1991 Vit et al. ................................ 623/16
5,047,031 9/1991 Constantz ............................. 606/77

Primary Examiner—Thurman K. Page
Assistant Examiner—Peter F. Kulkosky
Attorney, Agent, or Firm—Frank J. Uxa

[57] ABSTRACT

Hard tissue replacement materials and methods for making same are disclosed. In one embodiment, the present composition comprises a synthetically derived, substantially homogenous composite containing collagen component and calcium phosphate-containing component precipitated from a liquid medium in which the collagen component is contained.

17 Claims, No Drawings

COMPOSITE MATERIALS FOR HARD TISSUE REPLACEMENT

BACKGROUND OF THE INVENTION

This invention relates to composite materials for hard tissue replacement, and to methods for producing such materials. More particularly, the invention relates to collagen-containing composites, substrates coated with calcium, phosphate-containing components and methods for producing same. The collagen-containing composite materials can be prepared by precipitation of calcium, phosphate-containing materials, such as calcium apatite materials, in a collagen slurry. The coated calcium, phosphate-containing substrates can be prepared by contacting an uncoated substrate in a supersaturated or oversaturated solution of coating materials, such as calcium apatites, to coat the surface of the substrate.

The composition of hard tissue, such as natural bone, comprises collagen and inorganic calcium phosphate, particularly biological apatite. Bone contains about 60% to 75% by weight of biological apatite and tooth has more than 98% by weight of biological apatite. Biological apatite is a naturally occurring calcium apatite-type material which is formed in the body by precipitation from body fluids at body conditions. This biological apatite has a structure which is similar to pure hydroxyapatite, but contains some substitute ions for the calcium, phosphate and hydroxyl ions. Strictly speaking, synthetically produced precipitated hydroxyapatite is more similar to biological apatite than are the hydroxyapatite ceramics.

Synthetically produced precipitated hydroxyapatite is a very fine powder. It has limited application as a hard tissue implant material because it is somewhat difficult to manipulate.

Recently, premolded collagen incorporated with a granule form of hydroxyapatite ceramic (HA) have been commercialized. In such collagen-HA composites, the collagen and hydroxyapatite ceramics form a completely heterogeneous mixture. In effect, the collagen serves as the binder system for the granules of the hydroxyapatite ceramics. Such heterogenous composite materials are completely different from the natural bone. It would be advantageous to provide a hard tissue replacement material which has an increased similarity to natural bone.

In the last decade or so, many calcium phosphate-containing ceramics and glasses have been prepared in granule form or block form for hard tissue substitute materials. Among these are hydroxyapatite ceramics, tricalcium phosphate ceramics and calcium, phosphate-containing bioglasses. Clinical studies have confirmed that hydroxyapatite ceramics and such bioglasses are very good biocompatible materials for use as artificial hard tissue implant materials. After implantation, hydroxyapatite ceramics and calcium, phosphate-containing bioglasses bond very strongly with bone.

The hydroxyapatite ceramics, as well as the bioglasses, are somewhat different from biological apatite. In general, hydroxyapatite ceramics and bioglasses after implantation take a certain amount of time to adjust to the body's environment. Biological apatite from new bone starts to grow and bind to the surface of these implant materials. For example, calcium, phosphate-containing bioglass, after soaking in body fluid, takes several weeks to form a precipitated hydroxyapatite surface layer. The time for the formation of a hydroxyapatite layer depends strongly on the composition of the bioglass. Clinical studies have showed that the bonding strength between the bioglass and the bone during the initial healing stage also depends on the rate of formation of this hydroxyapatite surface layer. In general, those bioglasses with a fast rate of formation of precipitated surface hydroxyapatite also show a strong bonding with bone. Even though untreated hydroxyapatite ceramics and bioglasses have excellent biocompatibility, it would be advantageous to provide additional biocompatibility and to provide hard tissue replacement materials which shorten the healing time.

SUMMARY OF INVENTION

New hard tissue implant materials and methods for producing same have been discovered. The present invention provides collagen-containing composite materials which have properties generally similar to natural bone. Moreover, these synthetic composite materials can be produced so as to substantially eliminate the risk of immune system reactions, which often cause implant failure if the implant is made of natural bone matter. Further, the present materials which comprise coated substrates facilitate healing, for example, reduce the healing time required relative to the use of uncoated implant materials or substrates, from implantation surgery.

In one broad aspect, the present compositions, which are useful as hard tissue replacement or implant materials, comprise synthetically derived, substantially homogenous composites containing collagen component and calcium, phosphate-containing component precipitated from a liquid medium in which the collagen component is contained. Methods for producing such implant materials are also disclosed and are within the scope of the present invention.

In another broad aspect of the invention, compositions, which are useful as hard tissue replacement or implant materials, comprise a substrate, preferably selected from calcium apatite ceramics, calcium, phosphate-containing bioglasses and mixtures thereof, and a precipitated coating material selected from calcium apatites (meaning to include therein, for example, calcium hydroxyapatite, calcium fluorapatite, calcium carbonateapatite and the like) and mixtures thereof deposited on at least a portion of the external surfaces of the substrate from a supersaturated or oversaturated solution of the coating material prior to the composition being implanted in the body of an animal. Methods for producing such implant materials are also disclosed and are within the scope of the present invention.

DETAILED DESCRIPTION OF THE INVENTION

For the preparation of the present collagen component, calcium, phosphate-containing component composites, any suitable collagen component may be employed. The preferred collagen component used in the present invention is type 1 collagen. In one embodiment, the solid collagen component is dispersed in an acidic liquid, preferably aqueous, medium to form a collagen component-containing slurry, for example, in the form of a gel. The concentration of collagen component in this slurry is preferably in the range of about 0.5% to about 3% by weight. Either a calcium-containing component, e.g., salt, or a phosphate-containing component, e.g., salt, may be combined in, preferably dissolved in, the collagen slurry. If a calcium-containing component is combined into the collagen slurry, the phosphate-containing component is separately combined in, preferably dissolved in, a liquid medium, preferably water, preferably to form a solution. Similarly, if the phosphate-containing component is combined into the collagen slurry, the calcium-containing component is separately combined in, preferably dissolved, in a liquid medium, preferably water, preferably to form a solution. Alternately, two separate liquid media, preferably solutions, one with the calcium-containing component and the other with the phosphate-containing component, can be prepared.

The pHs of the slurry and the liquid medium are preferably adjusted to a level of about 7 or higher, preferably about 10 or higher. If the slurry and two liquid media (one including the calcium-containing component and the other including the phosphate-containing component) are used, the two liquid media (and the combined slurry/liquid media) are preferably adjusted to a pH of about 7 or higher, more preferably to a pH of about 10 or higher. In this instance, the slurry itself is preferably maintained acidic to better disperse the collagen. The slurry and medium (or media) are then combined or mixed together. Before and during this mixing, the slurry and the combination or mixture are preferably subjected to agitation or strong stirring, for example, with a blender or other conventional mixing machine. The liquid medium is (or liquid media are) preferably added quickly to the stirred slurry. This mixing is conducted at conditions effective to cause the formation and precipitation of a calcium, phosphate-containing component, for example, hydroxyapatite.

Without wishing to limit the invention to any particular theory of operation, it is believed that the precipitated calcium, phosphate-containing component interacts with the collagen component to form a substantially homogeneous material. After the mixing is completed, the resulting collagen-containing material is separated and purified, for example, by being filtered and/or centrifuged and/or washed several times with pure water until free of other components, such as entrapped soluble and insoluble impurities. The wet solid, e.g., filter cake, can then be shaped and dried, for example, by freeze drying, air drying, oven drying and the like, to form a bone-like composite material or a porous material. In order to enhance the mechanical strength of the final product, a collagen cross-linking reagent can be added into the slurry before separation and purification. If a collagen cross-linking agent is employed, the slurry is maintained for a sufficient period of time at conditions effective to obtain the desired cross-linking of the collagen component.

In order to induce the precipitation of a calcium apatite-like material in the collagen slurry, the preferred mole ratio of calcium to phosphate is about 1 to about 2, more preferably about 1.67. However, other mole ratios are also acceptable. Such other mole ratios of Ca to P are especially useful when the pH of the combined mixture is in the range of about 10 or higher.

The present collagen component, calcium, phosphate component-containing composites may have widely varying compositions provided that such composites are useful in the intended application. Preferably, such composites comprise about 25% to about 95% by weight of collagen component and about 5% to about 75% by weight of calcium, phosphate-containing component. The calcium, phosphate-containing component included in the present composites is preferably selected from calcium phosphates, calcium apatites (meaning to include therein calcium hydroxyapatite, calcium fluorapatite, calcium carbonateapatite and the like apatite-type materials) and mixtures thereof. Composites including calcium fluorapatite can be produced by including fluoride (fluoride ion) in one or more of the materials used to produce the present composites. The present composites may include one or more additional components useful to provide one or more desired properties to the composites. Metals, such as alkali metals, other alkaline earth metals and the like, may replace at least a portion, for example, a minor portion, of the calcium. At least a portion, for example, a minor portion, of the phosphate and/or hydroxyl contents of the calcium, phosphate-containing material may be replaced by halogen, such as chloride, fluoride and the like, carbonate and the like. The precipitated calcium, phosphate-containing material can have a chemical composition which resembles or even simulates that of biological apatite. Different components may be added to one or more of the materials (e.g., slurry and liquid medium or media) used to make the present composites to adjust the chemical composition of the product composite, as desired.

Any suitable, preferably soluble and more preferably water soluble, calcium-containing component may be employed in the present methods for making collagen-containing composites, provided that such calcium-containing component functions as described herein and results in a useful collagen-containing composite in accordance with the present invention. Such calcium-containing component is preferably substantially free of phosphorus. Calcium-containing salts and mixtures thereof are particularly useful. Examples of calcium-containing salts include calcium acetate, other soluble calcium carboxylates, calcium chloride, calcium nitrate, other soluble calcium organic salts and mixtures thereof.

Any suitable, preferably soluble and more preferably water soluble, phosphate-containing component may be employed in the present methods for making collagen-containing composites, provided that such phosphate-containing component functions as described herein and results in a useful collagen-containing composite in accordance with the present invention. Such phosphate-containing component is preferably substantially free of calcium. Phosphate-containing salts and mixtures thereof are particularly useful. Examples of phosphate-containing salts include alkali metal phosphate salts, ammonium phosphate salt and mixtures thereof.

While any suitable liquid medium may be employed (for example, for the slurry and/or the solution or solutions), the use of aqueous liquid media is much preferred. Various different materials may be employed to maintain or adjust the pH of the slurry and/or liquid medium or media, as desired. Examples of useful pH adjusting agents include alkali metal hydroxides, ammonium hydroxide and mixtures thereof. The slurry can be made acidic using any suitable acid which provides the desired acidity and does not unduly interfere with the methods and products of the present invention. Examples of such acids include acetic acid, other carboxylic acids and mixtures thereof.

In the present collagen-containing composites, the weight ratio of total calcium, phosphate-containing component to the amount of collagen component is preferably in the range of about 0.03 to about 2.5.

The present collagen-containing composites are different from previous collagen-calcium phosphate ceramic composite materials. The later are simply physical mixtures with collagen as binder for the calcium phosphate ceramics. No interaction between the collagen and the calcium phosphate ceramics occurs. In contrast, the present composites contain a calcium, phosphate-containing component which is incorporated into the structure of the collagen component, and is preferably interacted with the collagen component. The present composites are substantially homogenous, preferably with little or no phase separation being visually apparent. The present composites have substantial compositional flexibility and the weight ratio of precipitated calcium, phosphate-containing component to collagen component can be varied over a relatively wide range. By doing this, the mechanical strength and/or bioresorption rate of the present composites can be varied over relatively wide ranges. In addition, the present composites, which contain precipitated calcium apatite incorporated into collagen structure, have properties which are similar to the properties of natural bone.

It should be noted that in this invention the order of precipitation is quite important. For example, if calcium apatite is formed in the collagen free solution, the addition of this calcium apatite into a collagen slurry still shows two phases of materials including collagen and a separate phase of calcium apatite. This is different from the present substantially homogeneous composite materials.

The hydroxyapatite ceramics, other apatite ceramics and calcium, phosphate-containing bioglasses are normally prepared by sintering techniques at high temperatures. In one embodiment of the present invention, a substrate, preferably made from a material selected from calcium apatite ceramics, calcium, phosphate-containing bioglasses and mixtures thereof, is contacted with, preferably immersed or soaked in, an oversaturated or supersaturated solution, preferably an aqueous solution, of a coating material selected from calcium, phosphate-containing components, preferably selected from calcium apatites and mixtures thereof, preferably at a pH of about 6.5 or about 7.0 or higher. This contacting results in a coating of precipitated material selected from calcium, phosphate-containing components, preferably selected from calcium apatites and mixtures thereof, being deposited on at least a portion of the external surfaces of the substrates.

Suitable such oversaturated solutions can be prepared by mixing a calcium ion-containing solution and a phosphate-containing ion-containing solution. The total calcium concentration of such oversaturated solutions is preferably in the range of about $1.0 \times 10^{-3}$ M to about $3.0 \times 10^{-3}$ M and the total phosphate concentration of such oversaturated solutions is preferably in the range of about $1.0 \times 10^{-3}$ to about $2.0 \times 10^{-3}$ M.

Suitable calcium salts for the preparation of such oversaturated solutions are, for example, soluble calcium salts, such as calcium chloride, calcium nitrate, calcium acetate, other soluble calcium carboxylates, other soluble calcium organic salts and mixtures thereof. Suitable phosphate salts for the preparation of such oversaturated solutions are alkali metal phosphate salts, ammonium phosphate salts and mixtures thereof. Specific examples include monobasic alkali metal phosphates, dibasic alkali metal phosphates, tribasic alkali metal phosphates and mixtures thereof. pH adjusting agents such as alkali metal hydroxides, ammonium hydroxide and mixtures thereof may be employed.

The solubility of calcium apatites and other calcium phosphate salts is very sensitive to the pH of the liquid medium. In general, solubility of calcium apatites and other calcium phosphate salts decreases with increasing pH. The metastable limit of a calcium apatite oversaturated solution also decreases with increasing pH. In principle, any oversaturated solution can be used for contacting the present substrates to induce the precipitation of one or more calcium, phosphate-containing components, e.g., calcium apatites, on the substrate's surface. However, it is preferred to employ a stable metastable solution. By contacting the substrate with such a solution, the precipitated calcium, phosphate-containing component is deposited preferentially on the surfaces of the substrate rather than in the bulk of the solution. If the solution is excessively oversaturated, the solution is very unstable and bulk precipitation occurs immediately. In this case, the solution concentration decreases rapidly to the normal or saturated solubility values and the chances of deposition on the substrate surface are reduced.

The oversaturated solutions can be prepared by mixing required amounts of calcium ion- and phosphate ion-containing solutions at low pH (pH<6.0). At this low pH, the combined solution is undersaturated. The solution pH is then raised, preferably to 6.5 or about 7.0 or higher, for example, with diluted alkaline solution, until it reaches the metastable oversaturated region. The substrate can then be contacted with such solution. This contacting step can be repeated several times by using a different, for example, newly prepared, oversaturated solution for each contacting until the external surfaces of the substrate are covered by the desired amount of deposited precipitated calcium, phosphate-containing component. Other soaking methods which may be employed include the continuous flow of a metastable oversaturated solution to a reactor tank which contains the substrate for treatment. The contacting or contactings preferably continue until the newly formed precipitated material is attached to the surface of the substrate. The contacting solution is preferably maintained in the oversaturated condition during the treatment.

Because the precipitated calcium, phosphate-containing component, e.g., one or more calcium apatites, is more close to the biological apatite than the sintered calcium apatite ceramics or calcium, phosphate-containing bioglasses, the present coated substrates interact and bond with bone more quickly than do the uncoated substrates. Therefore, the healing time is shortened and the ceramic-bone bonding strength is stronger using the present coated substrates relative to the uncoated substrates.

The oversaturated solutions may contain some fluoride ion which induces the deposition of fluorapatite instead of hydroxyapatite. In such cases, the fluoride ion is preferably contained in the phosphate-containing solution before mixing with the calcium-containing solution.

Pure hydroxyapatite ceramic has a surface pH normally ranging from about 7.0 to about 10.0. In order to accelerate the formation of precipitated calcium apatite or fluorapatite on the surface of such ceramics, the ceramics can be prepared to include about 0.5% to about 3% unreacted calcium oxide. Ceramics which include excess calcium oxide normally have a surface pH of about 11 or higher. By introducing this ceramic into an aqueous solution, the unreacted lime leaches out and provides calcium ions and high surface pH, which are favorable conditions for the deposition of precipitated calcium apatites. In such case, the formation of precipitated calcium apatites on the surfaces of the substrate is faster than on substrates made of pure hydroxyapatite ceramics. The oversaturated solution for treatment can be the same as before. However, in certain circumstances, if the leachable calcium ion is high enough, the solution for treatment can only have phosphate ion or phosphate ion with fluoride ion.

The following non-limiting Examples illustrate certain embodiments of the present invention.

EXAMPLE 1

2 g of solid collagen (type 1 collagen obtained from ReGen Corporation) was added into 400 ml water and stirred. 0.5 ml glacial acetic acid was then added to this aqueous mixture and stirred. At this point, the slurry was in the form of a homogeneous gel. 4.4 g $CaCl_2$ anhydrous solid was then dissolved into the collagen gel. The pH of the mixture was adjusted to higher than 10 by adding $NH_4OH$.

3 g $(NH_4)_2HPO_4$ was separately dissolved in 30 ml of pure water.

The ammonium phosphate solution was added quickly into the above-noted collagen-containing slurry and the slurry was mixed vigorously in the blender.

The slurry is then filtered and the recovered solid material was washed several times with deionized water. The washed solid material was shaped and dried in air (with heat).

After drying, the dried material was visually examined and did not show separate phases of collagen and calcium phosphate. This dried material, which was about 33% by weight collagen and about 67% by weight calcium apatite, became very hard and did not show as much swelling in water as did pure collagen.

This dried material is useful as a hard tissue, e.g., bone, replacement material.

EXAMPLE 2

4 g of collagen (type 1 collagen derived from ReGen Corporation) was dispersed in 200 ml water containing about 0.5 ml of acetic acid to produce a slurry in the form of a homogenous gel.

2.2 g of $CaCl_2$ was dissolved in 10 ml of water. This solution was added to the above-noted slurry and stirred. The pH of the resulting slurry was adjusted with $NH_4OH$ to higher than 10.

1.7 g $(NH_4)_2HPO_4$ was dissolved in 15 ml of water.

The $(NH_4)_2HPO_4$ solution was added to the above-noted slurry and the slurry was strongly mixed in a blender.

The slurry was filtered, and the recovered solid material was washed several times with deionized water. The washed solid material was collected and shaped, and then air dried.

The final composite, which included about 67% by weight collagen and 33% by weight calcium phosphate, was very homogenous. No separate phases of collagen and calcium phosphate were observed This dried material is useful as a hard tissue, e.g., bone, replacement material.

While this invention has been described with respect to various specific examples and embodiments, it is to be understood that the invention is not limited thereto and that it can be variously practiced within the scope of the following claims.

What is claimed is:

1. A composition useful as a hard tissue replacement material comprising a synthetically derived, substantially homogenous, solid composite consisting essentially of about 25% to about 95% by weight of collagen component and about 5% to about 75% by weight of calcium, phosphate-containing component precipitated from an aqueous liquid medium in which said collagen component and a soluble calcium-containing component and a soluble phosphate-containing component from which said calcium, phosphate-containing component is derived are contained, said aqueous liquid medium prior to said precipitation being free of insoluble calcium-component and insoluble phosphate containing component.

2. The composition of claim 1 wherein said collagen component is type 1 collagen.

3. The composition of claim 1 wherein said calcium, phosphate-containing component is selected from the group consisting of calcium phosphates, calcium apatites, and mixtures thereof.

4. The composition of claim 1 wherein the mole ratio of calcium to phosphate is in the range of about 1 to 2.

5. A method for producing a collagen-calcium, phosphate-containing substantially homogeneous solid composite comprising:

forming a mixture containing aqueous liquid, collagen, and either a soluble calcium-containing component or a soluble phosphate-containing component;

combining said mixture with an aqueous liquid containing said soluble calcium-containing component or said soluble phosphate-containing component which is not present in said mixture, and subjecting said combination to conditions effective to cause the precipitation of a calcium, phosphate-containing component derived from said soluble calcium-containing component and said soluble phosphate-containing component, said combination prior to said precipitation being free of insoluble calcium-containing component and insoluble phosphate containing component; and recovering from said collagen and said precipitated calcium, phosphate-containing component a solid collagen-calcium, phosphate-containing material consisting essentially of about 25% to about 95% by weight of collagen and about 5% to about 75% by weight of said calcium, phosphate-containing component.

6. The method of claim 5 wherein said combination is agitated while being subjected to said conditions.

7. The method of claim 5 wherein said conditions include a pH of at least about 7.

8. The method of claim 5 wherein said conditions include a pH of at least about 10.

9. The method of claim 1 wherein said solid collagen-calcium, phosphate-containing material is a substantially homogenous solid composite.

10. The method of claim 9 wherein said recovering step comprises separating said solid collagen-calcium phosphate-containing material from one or more components other than collagen and said precipitated calcium, phosphate-containing component present with said collagen-calcium, phosphate-containing material.

11. The method of claim 10 wherein said recovering step further comprises drying said solid collagen-calcium, phosphate-containing material.

12. A method for producing a collagen-calcium, phosphate homogeneous solid composite comprising:

forming a mixture containing an aqueous liquid and collagen;

simultaneously combining said mixture with a first aqueous liquid containing a soluble calcium-containing component and with a second aqueous liquid containing a soluble phosphate-containing component at conditions effective to cause the precipitation of a calcium, phosphate-containing component derived from said soluble calcium-containing component and said soluble phosphate-containing component, provided that said mixture, said first aqueous liquid and said second aqueous liquid prior to said precipitation are free of insoluble calcium-are free of insoluble calcium-containing component and insoluble phosphate-containing component; and recovering from said collagen and said precipitated calcium, phosphate-containing component a solid collagen-calcium, phosphate-containing material consisting essentially of about 25% to about 95% by weight of collagen and about 5% to about 75% by weight of said calcium, phosphate-containing component.

13. The method of claim 12 wherein said first aqueous liquid and said second aqueous liquid each have a pH of at least about 7.

14. The method of claim 12 wherein said first aqueous liquid and said second aqueous liquid each have a pH of at least about 10.

15. The method of claim 12 wherein said solid collagen-calcium, phosphate-containing material is a substantially homogenous solid composite.

16. The method of claim 15 wherein said recovering step comprises separating said solid collagen-calcium, phosphate-containing material from one or more components other than collagen and said precipitated calcium, phosphate-containing component present with said collagen-calcium, phosphate-containing material.

17. The method of claim 16 wherein said recovering step further comprises drying said solid collagen-calcium, phosphate-containing material.

* * * * *

UNITED STATES PATENT AND TRADEMARK OFFICE
CERTIFICATE OF CORRECTION

PATENT NO. : 5,320,844
DATED : June 14, 1994
INVENTOR(S) : Liu

It is certified that error appears in the above-indentified patent and that said Letters Patent is hereby corrected as shown below:

Column 8, claim 9, line 60; delete "1" and insert in place thereof --5--.

Column 8, claim 10, line 63; delete "9" andinsert in place thereof --5--.

Column 9, claim 12, line 18; delete "are free of insoluble calcium-".

Signed and Sealed this

Twenty-first Day of March, 1995

Attest:

BRUCE LEHMAN

Attesting Officer     Commissioner of Patents and Trademarks